United States Patent [19]

King et al.

[11] Patent Number: 4,986,831
[45] Date of Patent: Jan. 22, 1991

[54] MEDICAL IMPLANT

[75] Inventors: Wendell L. King, North Oaks; Lawrence M. Kane, Roseville; Theodore P. Adams, Edina, all of Minn.

[73] Assignee: Angeion Corporation, Plymouth, Minn.

[21] Appl. No.: 186,002

[22] Filed: Apr. 25, 1988

[51] Int. Cl.$^5$ ............................................... A61F 2/06
[52] U.S. Cl. ........................................ 623/1; 606/151
[58] Field of Search ............................ 623/1, 12, 13; 128/334 R

[56] References Cited

U.S. PATENT DOCUMENTS

| | | | |
|---|---|---|---|
| 3,688,317 | 9/1972 | Kurtz | 623/1 |
| 4,190,909 | 3/1980 | Ablaza | 623/1 |
| 4,743,251 | 5/1988 | Barra | 623/1 |

FOREIGN PATENT DOCUMENTS

| | | | |
|---|---|---|---|
| 0217115 | 4/1987 | European Pat. Off. | 623/1 |
| 2001869 | 2/1979 | United Kingdom | 623/1 |

OTHER PUBLICATIONS

Gott et al.; "The Coating of Intravascular Plastic Prostheses with Colloidal Graphite", *Surgery*, vol. 50, #2, pp. 382–389, Aug., 1961.

*Primary Examiner*—Alan W. Cannon
*Attorney, Agent, or Firm*—Robert A. Elwell; Harold D. Jastram

[57] ABSTRACT

This invention is described and illustrated in connection with the generation of a homograft composed of collagenous tissue generated on a prosthetic device. A tubular substrate having generally cylindrical outside and inside surfaces is suspended in the lumen of a blood vessel of a living body. The tubular substrate is open at each end to permit blood to flow over both the inside and outside surfaces. One of the surfaces of the substrate is a thrombogenic surface or supports a thrombogenic mesh material to promote growth of a tube of collagenous tissue suitable for use as a surgical graft. The substrate is suspended in the blood flow of a blood vessel by an anchor which permits the substrate to freely move within the lumen of the vessel but is anchored by the tether to prevent the substrate from moving along the vessel in the direction of blood flow. The collagenous tissue growth about the substrate is generally tubular and suitable for use as a surgical graft.

The method of generating a homograft includes preparing a prosthesis composed of a tubular substrate. The substrate is open at each end to permit blood to flow along the length of the substrate inside wall. The substrate is selected to have at least one thrombogenic surface or a thrombogenic mesh material supported by the substrate. The prosthesis is inserted in the lumen of a blood vessel, either a vein or artery, of a living body and anchored in the lumen of the vessel to prevent the substrate from moving along the vessel with the blood flow. The body generates collagenous growth on the thrombogenic surface of the substrate while the substrate is freely suspended in the blood flow of the vessel. The substrate is then removed from the vessel after which a tubular homograft of collagenous tissue is removed from the substrate.

18 Claims, 3 Drawing Sheets a.  b.

c.  d.

e.  f.

g.  h.

i.  j.

MEDICAL IMPLANT

BACKGROUND

Vascular disease in man has become one of the primary causes of poor overall health and death in recent years. Vascular diseases occur throughout the body and affect the heart, limbs and other parts of the body. Arterial disease has caused death by heart attack, reduced physical activity due to constriction or blockage of vessels or arteries serving the muscles of the heart, and constriction or blockage of vessels and arteries to the limbs, particular to the legs. These vascular diseases have resulted in the loss of extremities when the blood flow becomes sufficiently restricted to prevent proper nourishment of the tissue of the extremities and have caused death when reduced blood flow to the muscles of the heart have starved the heart of needed blood.

Each year, hundreds of thousands of revascularization procedures for angina are performed in the world. Mild cardial revascularization and limb salvation which are well accepted procedures for treatment of arterial diseases depend upon a readily available supply of prostheses or vascular transplants for the purposes of returning proper levels of blood flow to affected parts of the body. The availability of a suitable vascular prosthesis or transplant is frequently a limiting factor in decisions to treat such diseases through surgical procedures, including coronary artery bypass surgery.

A variety of techniques and prostheses have been tried in an effort to provide a surgically applied prosthesis capable of restoring proper blood flow to the afflicted part of the body. Modern synthetic fabric technology has provided one form of prosthesis which has been tried as a substitute for diseased arteries and vessels. Such synthetic fabrics are woven into tubes of fabric which may be sutured to the ends of blood vessels in order to provide a bypass or a replacement for a diseased section of the vessel. Such prostheses present a number of problems for surgeons and for patients. Successful grafting of such fabric replacement prostheses requires an extended convalescence during which collagenous tissue generated by the body must become implanted in the fabric prosthesis in order to ensure a successful long-term graft. This lengthy convalescence exposes the patient to an extended period of time during which hemorrhage may occur in the prosthesis and at the site of the connection. Failure requires additional emergency surgical procedures. Further, there is always the danger that unfavorable reaction to the implanted fabric material will occur and prevent the long-term use of the fabric prosthesis in the patient.

Another procedure frequently adopted for the replacement of restricted and affected vascular sections involves the harvesting of venus grafts from other parts of the body. Commonly, sections of vessel are removed from the patient's legs and implanted in the coronary artery system. Surgical removal of vessels from the leg complicates the surgical treatment of coronary bypass procedures because the surgeon must in effect perform two surgical procedures. One procedure involves opening the chest cavity and the other involves harvesting the sections of vessel from the legs. This naturally increases the operative time associated wit vessel procurement with an increased danger to the patient Even successful bypass surgery of this type presents the patient with added distress during the recuperation period since healing must take place not only at the site of the surgical graft implant but also at the site of the harvesting of the vessel section.

A readily available supply of vascular grafts is desirable since emergency repair or grafting of arterial or venous sections must frequently be undertaken on relatively short notice. For this reason, one attempt to provide a readily available supply of such surgical grafts is outlined in U.S. Pat. No. 4,319,363 in which a vascular prosthesis and methods of making such a prosthesis are outlined. In this particular patent, the vascular prosthesis is generated in a non-human host. A tube of collagenous material reinforced by a fiber mesh is obtained through implantation in a non-human host and removed from the host after a predetermined growth of collagenous tissue has become implanted in the fiber mesh. After removal of the tube of fiber-impregnated collagenous tissue, the tissue is tanned in order to provide a source of a vascular prosthesis suitable for surgical grafting in human patients. An obvious disadvantage of such a vascular prosthesis involves a non-human host and therefore potential tissue incompatibility by a human patient. The patient on which such a graft is used may reject the foreign tissue since the non-human tissue is clearly a foreign body of a type commonly rejected by the human body.

In order to avoid tissue rejection, the best tissue available for vascular grafting is the patient's own body tissue. As indicated previously, one approach to using the patient's own tissue is to harvest vessel sections from the leg. Frequently, immediate replacement of constricted and diseased sections of arteries and vessels is not necessary. If sufficient time is available to the patient, tissue can be grown in the patient's own body in order to generate a tube of collagenous tissue which may be used as a graft. Charles Howard Sparks provided a method and apparatus for generating such tubes of collagenous material and these methods and devices are described in U.S. Pat. Nos. 3,866,609, 3,707,958 and 3,866,247. In these patents, Sparks describes a method and apparatus for generating tubes of collagenous material by forming a tunnel in muscle tissue located in or adjacent to the groin area of the body. A mandrel bearing a coat of fibrous material is inserted into the tunnel in the muscle tissue and surgically implanted in the muscle tissue for a period of time sufficient for the body to generate a growth of collagenous material which impregnates the fibrous material. The mandrel implant is then surgically removed from the surrounding muscle tissue for use as a vascular graft in the patient.

This method and the collagenous section of tube produced by this growth of collagenous tissue presents several disadvantages. First, the patient is required to undergo a rather extensive surgical procedure in the removal of the collagenous implant. The collagenous tube is generated as a tube which is thoroughly connected to and become a part of the surrounding muscle tissue. The collagenous tube must be very carefully removed from the surrounding muscle tissue before it may be used as a vascular graft. Further, the collagenous tissue generated by this procedure is muscle tissue and therefore a type of collagenous tissue which is characteristic of muscle tissue. It is not characteristic of the tissue normally associated with artery and vessel walls.

Medical investigation has revealed that there are noticeable differences between collagenous tissue generated in muscle tissue and collagenous tissue which is generated in or near the vascular system. While the collagenous tissue generated in the muscle tissue of a patient will be compatible with the patient's body tissues, it nevertheless is not of the same type of tissue normally associated with the vascular system and accordingly is not as desirable as a vascular graft as might be desirable.

Additionally, collagenous tubes formed in the muscle tissue may be nicked by the surgeon's instruments when removed and generally has walls of varying thickness. These walls of varying thickness can cause complications in the patient's circulatory system when such tissue is used as grafts.

Harvesting venous sections from other parts of the body also is less than satisfactory because the harvested sections are frequently of larger than optimum diameter. Small diameter transplants of good quality are difficult to obtain. Use of large diameter transplants results in difficult surgical procedures to connect the transplant because of this incompatability of size.

Thus it is apparent that past methods and apparatus for supplying vascular grafts have not been entirely successful. Such prior procedures and grafts have encountered problems with tissue rejection, extended convalescence, extended exposure to infection, lengthy surgical procedures and other risks attendant to coronary arterial bypass surgery and similar vascular graft surgery.

OBJECT OF THE INVENTION

It is therefore an object of the present invention to provide a method and apparatus for generating a homograft for implantation in a patient's body.

A further object of the present invention is to provide a method and apparatus for providing a tough and flexible small diameter homograft generated in the patient's own blood supply system for grafting in the patient's vascular system.

A further object of the present invention is to provide a method and apparatus for providing a fabric-reinforced homograft generated in the presence of a patient's blood flow in which collagenous tissue generated in the fabric is of the same type and quality characterized by the tissue of the patient's blood vessel walls.

A further object of the present invention is to provide a method and apparatus for generating a homograft in a vessel in the presence of a patient's blood supply to provide a vascular graft having a uniform wall thickness reinforced by a fabric mesh and in which the surface of the collagenous material is smooth and shiny with the characteristics of the cell structure characterized by the vessel walls of the patient.

Yet another object of the present invention is to provide a method and apparatus for generating a homograft in a vessel in the presence of blood flow in which a tubular substrate is suspended in the blood flow of a vessel and anchored at one end to prevent the substrate for moving along the length of the vessel in the direction of the blood flow while collagenous tissue grows on a thrombogenic surface of the substrate to provide a tube of collagenous tissue suitable for grafting in the patient's body for replacement of diseased sections of the patient's vessels or arteries.

Another object of the present invention is to provide for the growth of a tubular homograft in the presence of blood flow about a tubular substrate to produce a section of collagenous tissue which can be removed from the substrate and inverted so that the surface of the homograft exposed to the blood flow remains the surface expose to blood flow when the homograft is grafted as a bypass or a section of an artery or vessel in a patient's body.

These and other objects and advantages will become more apparent by reference to the following drawings.

THE DRAWINGS

FIG. 1 is a cross-sectional view of a tubular substrate according to the present invention shown with an attached anchor, FIG. 2 is a cross-sectional view of a substrate illustrated in FIG. 1 of the drawings with a fabric extending along the length of the substrate, FIG. 3 is a cross-sectional view of a substrate according to the present invention illustrating a substrate as illustrated in FIG. 1 of the drawings having a coated fabric extending along the length of the substrate, FIG. 4 of the drawings is a cross-sectional view of a substrate illustrated in FIG. 1 of the drawings illustrating a fabric extending along an outside surface and an inside surface of the substrate, FIG. 5 of the drawings is a cross-sectional view of a substrate according to the present invention illustrating a tube of fabric extending along an inner surface of the substrate and anchored at each end of the substrate, FIG. 6 of the drawings is a perspective view of a substrate according to the present invention illustrating a fabric extending over an outer surface of the substrate, FIG. 7 of the drawings is a perspective view of a substrate in accordance with the present invention illustrating a fabric covering an inside surface of the substrate, FIG. 8 is a cross-sectional view of a prosthetic device including a substrate according to the present invention tethered in the lumen of a vessel, FIG. 9 is a cross-sectional view of a prosthetic device according to the present invention illustrating removal of a homograft from a substrate FIG. 10 is a cross-sectional view of a homograft produced in accordance with the present invention, FIG. 11 is a cross-sectional view of a homograft having varying wall thicknesses, FIG. 12 is a cross-sectional view of a prosthetic device with a mesh material positioned within a substrate, FIG. 13 is a cross-sectional view of a prosthetic device with a mesh material positioned within a substrate and stretched along a longitudinal axis, FIG. 14 is a cross-sectional view of a prosthetic device illustrating a mesh material connected to ends of the device, and FIG. 15 is an illustration of a series of steps demonstrating implantation of a prosthesis in a vessel.

DETAILED DESCRIPTION OF INVENTION

Figure 1:
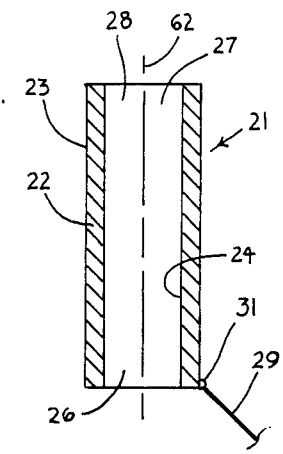

Refer first to FIG. 1 of the drawings which illustrates the simplest form of a prosthesis generally designated by the numeral 21 and which is illustrative of one form of a prosthesis 21 in accordance with the teachings of the invention. Prosthesis 21 is essentially a tubular substrate 22. Tubular substrate 22 has an outside wall 23 and an inside wall 24. The substrate 22 is generally cylindrical in shape and is open at each end. Open end 26 communicates with lumen 27 and permits blood to enter the substrate 22 to contact wall 24. Blood flow through substrate 22 exits at open end 28.

Substrate 22 can be made from a variety of products. Examples of non-thromgobenic material that can be used to form substrate 22 are carbon, carbon coated material, Cardiothane, Avcothane, heparinized coated material, albumin coated material, polyurethane or Biomer.

Substrate 22 is the base on which a homograft is generated according to the present invention as will here in after be more fully described.

Another important feature of prosthesis 21 is an anchor 29 which is connected to the substrate 22 near end 26 of the substrate 22. Anchor 29 can be attached to substrate 22 in a variety of ways, however, a simple method of attaching anchor or tether 29 is to apply a solvent or glue to a portion 31 of substrate 22. In the case where a solvent is used, a solvent should be selected which will dissolve a small portion of the substrate material 22. An end of the tether 29 can then be positioned in the dissolved portion. The tether 29 will then be secured to substrate 22 when the solvent evaporates and permits the material substrate 22 to resolidify. The tether 29 can be made of a number of materials including dacron, nylon, silk and polyester fiber, silk, polyethylene or similar materials which are suitable to be attached to substrate 22. A selection of material for tether 29 will be governed to some extent by the materials selected for constructing substrate 22. Tether 29 is preferably flexible and also is preferably non-thrombogenic so that when substrate 22 and tether 29 are positioned in the lumen of a vessel, collagenous tissue will not collect on the tether 29.

Prosthesis 21 is constructed so that it can be positioned, as will be more fully discussed hereinafter, within the lumen of a patient's vessel and anchored within the blood flow of the vessel by tether 29 so that blood will flow over surfaces 23 and 24. The prosthesis 21 is specifically designed so that the lumen 27 will permit blood flow in the vessel and thus not cause damage to the patient while a homograft is being generated on the substrate 22 by the growth of collagenous tissue.

In order to encourage growth of collagenous tissue on the substrate 22, either one or both of the surfaces 23 or 24 must be a surface which has thrombogenic characteristics. For instance, if substrate 22 is positioned within the lumen of a vessel for the purpose of generating a tube of collagenous tissue of a diameter of the same dimension as the diameter of outside surface 23, then surface 23 should have thrombogenic characteristics. Substrate 22 may also be selected so that the entire substrate 22 is constructed of thrombogenic material. In this case collagenous tissue will form on both the inside surface 24 as well as the outside surface 23. In most cases, however, it will be desirable to form a layer of collagenous tissue on only a single surface. Therefore, substrate 22 would preferably be formed of a non-thrombogenic material. The surface which is to be used to form a homograft, however, will be treated so that it will become a thrombogenic surface. If outside surface 23 is chosen to be the thrombogenic surface, then substrate 22 may be treated with a material which is thrombogenic.

Figure 10:
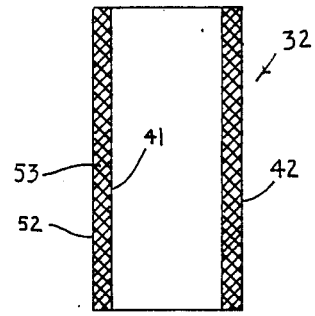

The finished homograft 32 is illustrated in FIG. 10 of the drawings. FIG. 10 illustrates a homograft 32 which has been generated on the surface of a substrate such as substrate 22 and has been removed from the substrate to provide a homograft 32 which can be used to replace diseased or clogged arterial or venus sections of a patient's body. The specific homograft illustrated in FIG. 10 of the drawings is shown with a mesh 33 which is formed as part of the homograft 32. It is not necessary to use a mesh material. Homograft 32 can merely be grown on the outside surface 23 or on the inside surface 24 of a substrate 22 by the methods incorporated in the present invention. Use of a mesh material 33, however, will be more fully described hereinafter and is contemplated as a version of the present invention.

Figure 8:
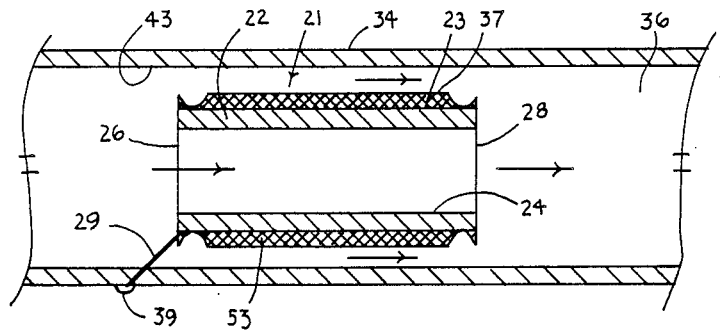

Next, refer to FIG. 8 of the drawings which demonstrates an important feature of the present invention. FIG. 8 illustrates a cross-sectional view of a vessel 34 with a prosthesis 21 positioned within the lumen 36 of the vessel. The prosthesis 21 is positioned to promote the growth of collagenous tissue 37 on the outside surface 23 of substrate 22. The collagenous tissue 37 becomes a homograft 32 after the collagenous tissue is removed from the outside surface 23 of the substrate 21.

An important feature of the invention is the positioning of prosthesis 21 in the lumen 36 of the vessel 34 so that blood will flow through the tubular substrate 22 and provide a continuous flow of blood over surfaces 23 and 24. Substrate 22 is specifically designed to be substantially tubular in shape so that the resulting homograft will be similar in cross sectional shape to a human vessel or artery. Blood flows in the arrow direction as illustrated in the drawings in FIG. 8 from left to right. The tubular shape of the substrate 22 thus permits a nearly unobstructed flow of blood in the lumen of the vessel so that no danger will be created for the host when substrate 22 is suspended in lumen 36.

As might be expected, blood flow through vessel 34 will tend to force substrate 22 to move along vessel 34 in the direction of the blood flow. In order to prevent such movement of the substrate 22, a tether 29 is provided to anchor the substrate and prevent movement of the substrate 22 with the blood flow. As indicated, tether 29 is preferably a flexible material which will permit the tether 29 to be anchored through the vessel wall 38. In a preferred embodiment, tether 29 is simply surgically tied off in the tissue outside the wall of vessel 34 and is tied surgically at point 39 in the patient's muscle or connective tissue.

A vein is chosen as the preferred site for generating a homograft using the prosthesis 21 and method of this invention because it provides several important safety features for the host. First, a prosthesis 21 may be implanted in a vein with relative ease because the pressure developed in a vein is relatively much lower than the blood pressure which is present in an artery. Consequently, the prosthesis 21 can be surgically implanted within the lumen 36 of a vein without exposing the host to dangerous loss of blood which might occur if such an implant is attempted in an artery. Further, it has been found that the prosthesis 21 can be implanted in the lumen 36 of a vein with the assurance that the opening caused by the implant can be surgically closed and will heal with very little difficulty.

A further important reason for selection of a vein as the implant vessel of first choice is that in the event tether 29 should fail, movement of substrate 22 along the lumen 36 of vein 34 will not result in excess danger to the host. In the event that a failure of the tether should occur, the prosthesis 21 will merely move along the lumen 36 until it encounters a passage too small for it to move further. In other words, it will become "filtered out" by some other portion of the body. In the case of a vein, the filtering system ultimately becomes the lungs. A blockage created by a failure of the prosthesis, tether 29, would not cause excessive danger to the host since the blockage in a lung or some other body part involving a vein is relatively easy to correct and is not normally life threatening to the host.

An artery is another possible choice for the implant but is less desirable than a vein. An artery presents certain disadvantages because failure of the prosthesis as described could possibly result in the prosthesis moving along the lumen of an artery to a point where it is blocked in an artery leading to the heart. This, of course, could be a potentially troublesome blockage which could cause circulatory problems for the host. Nevertheless, with proper precautions and careful monitoring of the patient, the choice of an artery is a perfectly acceptable site for implant.

Refer again to FIG. 8 of the drawings. In a properly implanted prosthesis 21, the tether 29 restricts the movement of substrate 21 within the lumen 36 of vessel 34 so that blood flows along inside surface 24 as well as outside surface 23. As illustrated in FIG. 8 of the drawings, the outside surface 23 can be prepared by the addition of additional material so that outside surface 23 is a thrombogenic surface and encourages the growth of collagenous tissue. This collagenous tissue growth takes the shape of outside surface 23. A preferred surface shape, of course, is substantially tubular and of a diameter which is designed to specifically match the diameter of a vessel or artery which is the subject of corrective implant surgery in the patient. A surgeon can first determine the approximate diameter of an obstructed artery in the patient. From this determination, the surgeon can then select a substrate 22 having an outside diameter 23 of approximately that necessary to match the portion of an artery to be surgically removed from the patient. Prosthesis 21 can be utilized to grow a homograft 32 in the patient's own blood supply. This homograft 32 will be totally compatible with the patient's tissue since the homograft 32 is composed of the patient's own tissues.

Further, it has been found that because the homograft 32 is grown in the patient's own blood supply the inside surface 41 and the outside surface 42 of the homograft 32 will have the same cell structure as the walls 43 of the patient's own vessel 34. This is an important aspect of the present invention because research has revealed that the collagenous tissue generated in various parts of the body has different cell structures. The cell structure of tubes of collagenous tissue generated in muscle tissue take on the characteristics of the cell structure of muscle tissue. This collagenous material is different from the cell structure of collagenous tissue generated in the cardiovascular system of the same host. Consequently, growth of a homograft 32 within the blood supply of a patient generates collagenous tissue which contains the same cell structure as the walls 43 of the patient's vessel 34. Thus, a homograft 32 generated within the patient's own vessels produces the perfect surface for carrying blood since it is composed of collagenous tissue having the cell structure compatible with blood flow. The collagenous tissue generated using the methods of this invention and the apparatus described herein has been found to be extremely tough living tissue having a shiny wall. Characteristics of this type are also noted as the same characteristics as those demonstrated by the inside wall 43 of vessel 34. Consequently, a homograft 32 is produced which is highly compatible with the patient's own blood vessel tissue.

Generation of a homograft 32 in the vessel in the presence of blood flow has been discovered to have an additional benefit. Collagenous tissue will begin to form on a thrombogenic surface as a reaction to body functions which tend to isolate the foreign body characterized by substrate 22. It has been found, however, that in many prior art methods, the collagenous tissue generation is nonuniform. Desirable replacements for vessels and arteries include a homograft which is of uniform wall thickness. Prior art methods for generating homografts have promoted such growth in muscle tissue where the homograft must be surgically removed from the surrounding muscle tissue. It has been learned from experience that such a homograft will have varying wall thicknesses along the length of the homograft. An illustration of such a homograft is set forth in FIG. 11 of the drawing.

Figure 11:
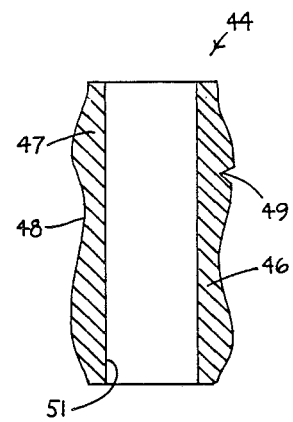

FIG. 11 illustrates a tube of collagenous material produced according to prior art practices. It is noted that this FIG. 11 is in cross-section to show a wall 46 which has varying thicknesses. Wall 46 is generated of collagenous material which might, as an example, be generated in or near muscle tissue. The collagenous tissue is not of uniform thickness and, therefore, produces a wall having thicknesses such as that illustrated by wall 46.

Further, when such a collagenous growth is removed from surrounding muscle tissue, the removal process requires surgically cutting away muscle tissue from the collagenous tissue. This surgical procedure will produce varying thicknesses in the wall 46. Thick portions 47 may be produced in the wall 46 with adjacent thinner portions 48 of the wall. Further, surgical removal may result in the surgical instrument producing nicks 49 in the wall 46. Consequently, such surgery results in a finished tube 44 which contains a variety of wall thicknesses, nicks and other imperfections which diminishes the value of the tube 44 as a surgical implant.

Further, when a tube 44 of the type illustrated in FIG. 11 is implanted, the body tends to compensate for varying wall thicknesses. The thin portion 48 may be a potential site of a rupture. The patient will be exposed to potentially catastrophic loss of blood from any such rupture. Further, the human body tends to compensate for weaknesses in the walls of blood vessels and it has been proposed that the unevenness will be compensated by tissue growth in the weaker areas so that the interior surface 51 of such a tube 46 will become uneven when the body attempts to compensate for weaknesses in the tube wall 44 at thin portion 48 or at nick 49. This, of course, produces a less than desirable final result since a smooth shiny uniform interior wall is desired in the transplanted graft. A homograft made according to the present invention does not produce a tube of collagenous tissue with the unevenness potentially described in FIG. 11 of the drawings since it has been found that the collagenous tube or homograft 32 generated by the process of the present invention contains a wall 52 of uniform thickness.

Figure 2:
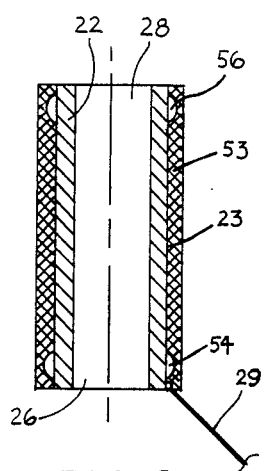
Figure 6:
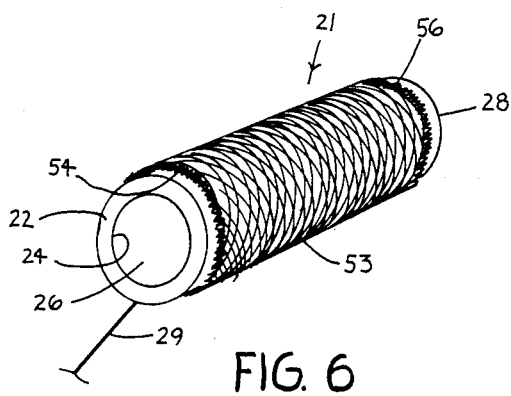

Refer next to FIGS. 2 and 6 of the drawings which illustrate an additional feature of the invention. A homograft implanted in the cardiovascular system is immediately subjected to fluid pressure. This pressure places stress on the implant. Consequently, a homograft having enhanced structural strength is often desired for implant in a patient. To accommodate this need, a homograft is generated according to the present invention by promoting growth of collagenous tissue about a structure of synthetic material. This synthetic material will strengthen the homograft walls and insure that the homograft will not rupture through prolonged use in the patient.

FIGS. 2 and 6 illustrate the use of a mesh tube 53 which is placed over outside surface 23 of substrate 22. Mesh tube 53 is preferably a woven tube of material which is easily supported by substrate 22. Tube 53 is secured near open end 28 by attaching tube 53 to the substrate 22 near open end 28. The tube 53 is then extended along the length of substrate 22 along the outside surface 23 and is secured at point 54 near open end 26 to the substrate 22.

Preferably, mesh material 53 is loosely connected between points 54 and 56 so that blood flow in the lumen 36 can circulate throughout the mesh material, including the surfaces of the mesh material adjacent the outside surface 23 of substrate 22. Mesh material 53 is a thrombogenic material which encourages the growth of collagenous tissue throughout the mesh to produce a homograft of superior strength. Collagenous tissue will completely impregnate the mesh and will also coat the inside and outside surfaces to produce a homograft as illustrated in FIG. 10 of the drawings. In FIG. 10 of the drawings it is noted that mesh material 53 is completely covered by collagenous tissue so that the inside surface 41 and outside surface 42 of the homograft 32 is composed of collagenous tissue of the host body. The mesh material 53 can be constructed of a variety of thrombogenic materials. Preferably the braid, mesh or knit materials, including dacron; monofilament nylon; silicone polyester fiber; silk; polyethylane or similar materials.

The mesh 53 can be anchored at points 54 and 56 to substrate 22 by applying a solvent to the substrate material 22 and holding the mesh material in contact with the dissolved area for a sufficient period of time to permit the solvent to evaporate leaving a hardened area represented by point 56. The mesh material can then be extended along outside surface 23 of substrate 22 to point 54 where the process is repeated thus anchoring the mesh 53 in the material of the substrate 22. Mesh material 53 should be extended along surface 23 so that it is not excessively tight and is permitted to be sufficiently loose so that blood flow as previously indicated can contact all surfaces of the mesh 53 to impregnate the material. Tether 29 can be connected to the mesh material 53 to provide the anchor means for securing the prosthesis 21 in the lumen 36 of the vessel.

Figure 3:
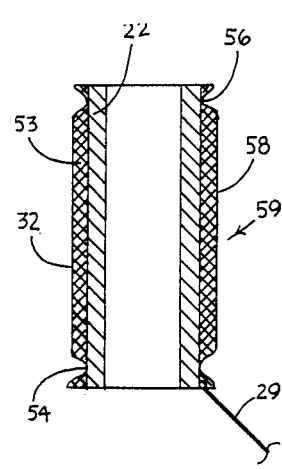

Refer now to FIG. 3 of the drawings which illustrates yet another variation of the present invention. In this particular version, the mesh material 53 is not an open weaved mesh which promotes impregnation of the collagenous material throughout the mesh 53. In this version, the mesh material 53 is first coated by a coating 58 of thrombogenic material. In effect, the prosthesis 21 employs a mesh material 53 which contains an impervious surface of thrombogenic material 58. Collagenous tissue is then generated on the outside of the coating 58 so that a thin coating of the collagenous tissue is generated on that surface. As will be explained more fully hereinafter, this version of the invention involves generation of only one collagenous tissue surface. The homograft is utilized by inverting the homograft 32 to produce a usable transplantable tube with the surface carrying the collagenous tissue being exposed to blood flow after it is inverted.

Figure 4:
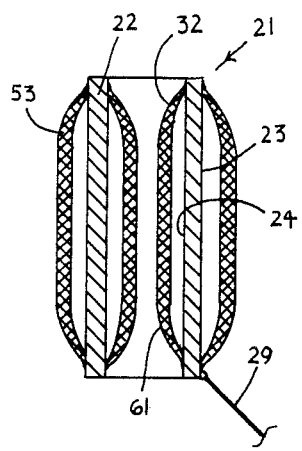

Patients who must undergo coronary bypass surgery frequently require multiple bypass procedures. Triple and quadruple bypass surgery is a common surgical procedure. Consequently, multiple sections of transplantable material are necessary to successfully complete such multiple transplants. It is not uncommon that the multiple bypass procedures will involve arteries of differing diameters. In situations such as that, homografts of differing diameters which closely match the diameter of the specific arterial bypass or replacement will require homografts of different diameter. FIG. 4 of the drawings illustrates a method and a prosthesis for generating homografts of differing diameters for making such quadruple procedures possible.

In FIG. 4 of the drawings, a mesh material 53 is extended along outside surface 23 of the substrate 22 just as illustrated in connection with FIGS. 2 and 6 of the drawings. This, of course, will produce a homograft 32 having an inside diameter of approximately the same diameter as the outside surface 23 of substrate 22. An additional homograft 32 may be generated simultaneously with a homograft on the outside surface of the substrate 22 by extending a mesh material 61 along the inside surface 24 of substrate 22. Mesh material 61 can be secured to substrate 22 as previously described in connection with the attachment of mesh 53 to the outside of substrate 22. In this fashion, substrate 22 supports mesh material 61 along an inside surface 24 and thus produces a homograft 32 of a substantially smaller diameter.

Generation of two homografts on the same substrate 22 is possible according to the present invention because blood flow is permitted to occur along the longitudinal axis 62 of the substrate 22 which has the opening 26 and 28 at either end of the substrate 22. Consequently, mesh material 53 and 61 are each surrounded by blood in the host vessel. This encourages thorough saturation of mesh material 53 and 61 by the blood of the host with the result that collagenous tissue will impregnate both of the tubes of mesh material and will then generate two homografts 32. Each homograft will be identical except that one will have a larger diameter.

Figure 5:
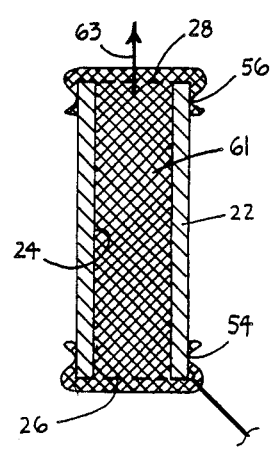
Figure 7:
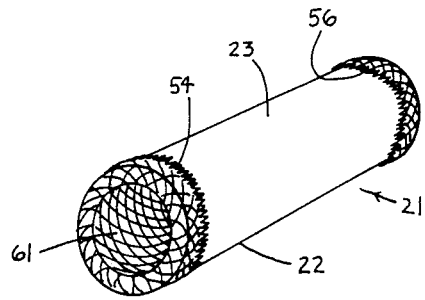

Reference to FIGS. 5 and 7 of the drawings will illustrate a method of generating a homograft 32 by merely supporting a mesh material 61 within the lumen 27 of substrate 22. In the variation of the invention illustrated in FIGS. 5 and 7 of the drawings, the mesh material 61 is extended beyond the open ends 26 and 28 and wrapped around the end of the substrate 22 and secured at point 54 and 56 of the substrate 22 in the same fashion that mesh 53 is secured to substrate 22. As will be apparent from reference to the drawings, material 61 is then supported along inside surface 24 of the substrate 22 so that blood can flow in the arrow direction 63 to encourage collagenous tissue growth on and in the mesh material thus producing a small diameter, homograft 32.

It is important that the mesh material 61 placed on the inside surface 24 of substrate 22 does not contact inside wall or surface 24 of substrate 22 too securely. A completely tight contact between the mesh material 61 and the inside surface 24 of the substrate 22 will inhibit or prevent free flow of blood over surfaces of the mesh material 61 which are in contact with inside surface 24. A preferred method of constructing a prosthesis 21 is illustrated in FIGS. 12 and 13 of the drawings when a homograft is to be produced utilizing the inside surface 24 of the substrate 22 as the support surface.

Figure 12:
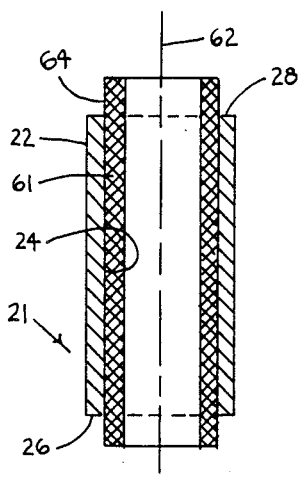
Figure 13:
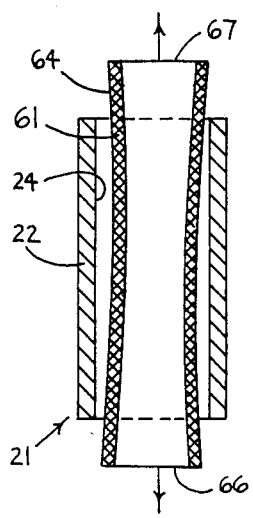

In FIG. 12, a mesh material is first inserted into substrate 22 and extended along the longitudinal axes 62 so that the mesh 61 extends beyond the opening 26 and the opening 28 at either end of tubular substrate 22. It will be noted that if the outside diameter of mesh 61 is sufficiently large, it will contact inside surface 24 of substrate 22 when mesh tube 61 is in a relaxed position. In order to mount mesh material 61 within substrate 22 but substantially so that outside surface 64 is supported by the substrate 22 out of contact with inside surface 24, the ends 66 and 67 are simultaneously pulled in the arrow direction as illustrated in FIG. 13 of the drawings. When this occurs, the tube of mesh material 61 will become elongated. Elongation of a mesh tube of material will reduce the diameter of the mesh material 61 so that its outside surface 64 is smaller in diameter than in its relaxed condition. While the mesh 61 is stretched, the ends 66 and 67 are then secured to substrate 22 as illustrated in FIGS. 5 and 7 of the drawings. In effect, mesh 61 is permanently supported within substrate 22 in a stretched condition with a reduced diameter. Blood flowing along the length of substrate 22 will then flow along all surfaces of mesh 61 including the area between the outside surface 64 of mesh 61 and the inside surface 24 of substrate 22. This will then promote the growth of collagenous tissue throughout the mesh 61 and will provide two shiny smooth surfaces of collagenous tissue completely surrounding the mesh material 61.

In the various illustrations of a prosthesis 21 consistent with the teachings of the present invention which utilize mesh material 53 or mesh material 61, the outside surface 23 and the inside surface 24 of substrate 22 should be nonthrombogenic to inhibit growth of collagenous tissue on those surfaces. By inhibiting growth of collagenous tissue on those surfaces of the substrate 22, the homograft can be more easily removed from the substrate 22.

Figure 9:
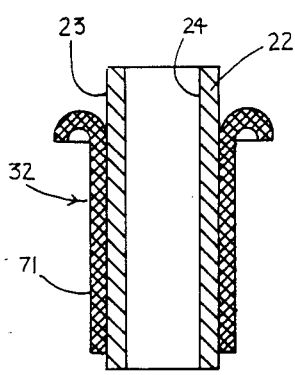
Figure 14:
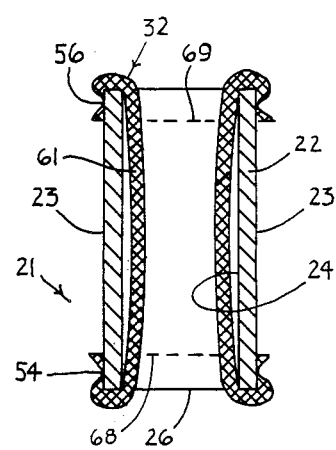

The method of removal of the homograft from the substrate 22 is illustrated in FIGS. 14 and 9 of the drawings. In FIG. 14, the version of the invention illustrating a homograft 32 generated within the lumen of a substrate 22 is illustrated. First, cuts are made up along the open ends 26 and 28 of the prosthesis 21 to remove the ends. For purposes of illustration, cuts are made along line 68 and line 69 of open ends 26 and 28 respectively. The cuts remove the ends of the substrate 22 along with the connection points 54 and 56. These are disposable portions of the prosthesis which cannot be used for implant purposes and, therefore, are discarded. After the prosthesis 21 is cut along lines 68 and 69, the homograft can easily be removed from the underlying substrate 22 which has nonthrombogenic surfaces.

In the case where the homograft is formed on the outside surface 24 of substrate 22 as illustrated in FIG. 9 of the drawings, the homograft 32 is shown being peeled away from the substrate 22. FIG. 9 illustrates a useful and unusual feature of the current invention. In the process of removing homograft 32 from the outside surface 23 of the substrate 22, the homograft 32 can be inverted. By inverting homograft 32, the outside surface 71 of the homograft 32 then becomes the inside surface of the homograft. When a homograft 32 is thus inverted, the surface 71 which was in contact with the greatest blood flow of the patient will then be in contact with the patient's blood flow after the homograft is implanted in the patient's circulatory system. This provides an obvious advantage. The very surface which was generated by the patient's own blood flow system and which is most compatible with the patient's own blood products will be the same surface exposed to the patient's blood flow when the implant is completed. This then promotes the compatible and natural employment of the patient's own body tissues for blood supply purposes.

The process involved in generating a transplantable homograft in accordance with this invention can broadly be outlined in three different phases. The first phase involves the preparation of the prosthetic device 21. Preparation of the prosthesis 21 has been outlined in connection with a description of the drawings including the various versions of the prostheses utilizing mesh material 53, attachment of the mesh material and the like.

The second phase of the process of generating a homograft of collagenous tissue involves the placement of the prosthesis 21 in the lumen of a vessel of a host. Again note that a vessel is chosen for the purposes of this invention because a vessel provides an adequate flow of blood for the purpose of generating the homograft and yet does not expose the host to the unusual risk of hemorrhage or the like. An artery is not a choice for a site of implant of the prosthesis 21 since the artery is a high pressure vessel which is difficult to treat. Implantation in an artery would expose the host to a high risk of hemorrhage and other complications including difficulty in closing an incision for a sufficient period of time to permit growth of collagenous tissue on the prosthesis 21. Accordingly, this invention contemplates the use of a vessel for the purpose of generating a homograft.

Figure 15:
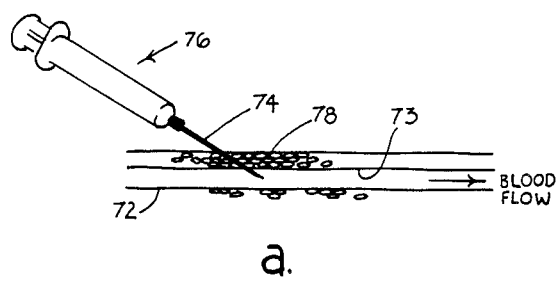
Figure 15:
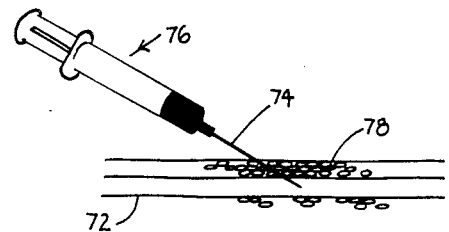
Figure 15:
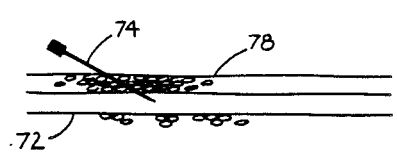
Figure 15:
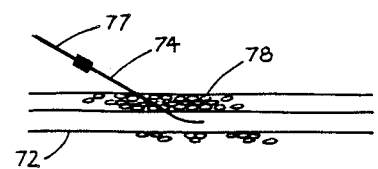
Figure 15:
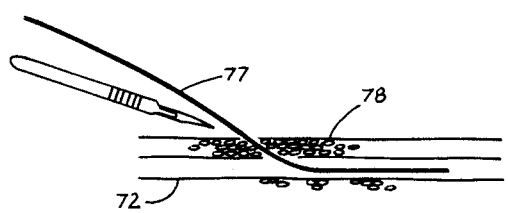
Figure 15:
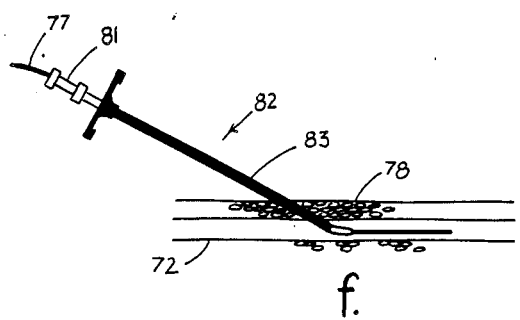
Figure 15:
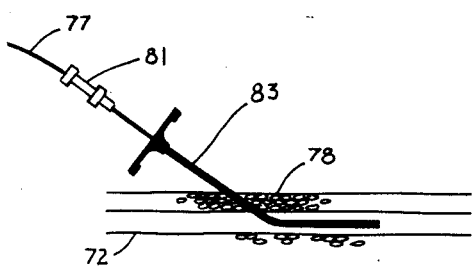
Figure 15:
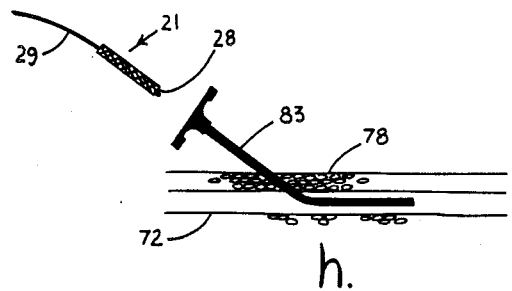
Figure 15:
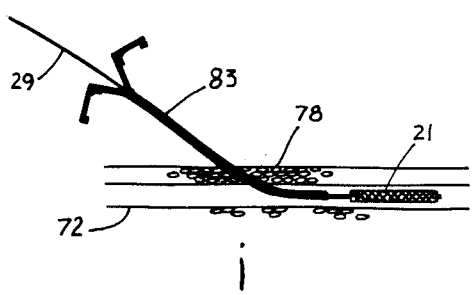
Figure 15:
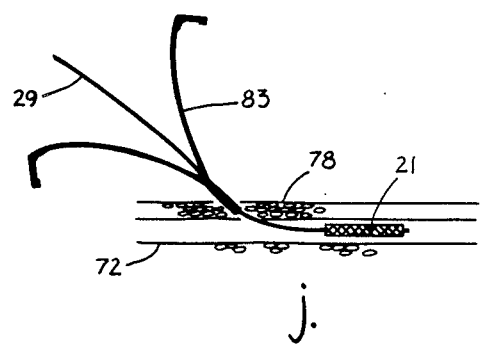

After the prosthesis 21 has been prepared according to the previous description, the prosthesis must be inserted in a vessel. A vessel such as the femoral vessel is selected for the implant of the prosthesis 21. The selected vessel should have a lumen diameter sufficiently large to permit the prosthesis 21 to be suspended in the blood flow of the vessel. FIG. 15 of the drawings is a multi-Figure drawing illustrating insertion of a of a prosthesis 22 into a vessel. First the vessel 72 is accessed by making an incision in the vessel wall 73. The incision in the vessel wall might be through a surgical incision process or it may be through the use of a needle 74 of a syringe 76. A preferred method of entering the vessel is illustrated in FIG. 15a and involves use of an extra-thin wall needle 74 and syringe 76 to enter the vessel 72. When this method is used for the incision, the needle of the syringe is inserted through the wall 73 of the vessel with the point of the needle generally pointed in the direction of the blood in the vessel.

Next, as illustrated in FIG. 15b, the vessel 72 is aspirated gently as the insertion of the needle 74 is completed. When the femoral vessel 72 has been entered, the syringe 76 is then removed from the needle leaving the needle in place as illustrated in FIG. 15c. A typical needle would be an 18-gauge syringe needle.

Next, a "J-wire" 77 is inserted through the needle 74 so that the wire 77 extends partially along the length of the lumen of vessel 72 leaving a portion of the wire exposed as illustrated in FIG. 15d. The needle is then removed from the vessel by moving the needle along the wire exposed outside of the vessel as illustrated in FIG. 15e.

Next, a small incision of approximately 2 centimeters is made at the point where the wire 77 exists from the vessel wall 73 and the surrounding tissue 78. The incision can be made with a scalpel 79.

Next, a vessel dilator 81 and introducer sheath 82 are threaded over the exposed portion of the wire 77 and firmly advanced along the length of the wire into the incision made in the vessel wall. This procedure is illustrated in FIG. 15f.

Next (see FIG. 15g), the vessel 81 dilator and the J-wire 77 are removed leaving the sheath 83 of the introducer in place. This leaves the one end of the sheath 83 in the lumen of vessel 72 and extending along the length of the vessel for a short distance. The remainder of the sheath 83 exposed outside the body. The sheath 83 provides a conduit for entering the vessel.

Prosthesis 21 is introduced into the sheath 83 and firmly advanced along the inside of the sheath, through the sheath and into the lumen 36 of the vessel where the prosthesis 21 is deposited in the lumen 36. This procedure is illustrated in FIGS. 15h and 15i.

The prosthesis 21 is oriented in the vessel so that the open end 28 is introduced into the vessel first. The prosthesis is directed through the sheath and is moved into the lumen 36 of the vessel 72 in the direction of the blood flow in the vessel. The opening 26 and the end of the prosthesis 21 connected to the tether 29 is the last part of the prosthesis 21 to be inserted through the wall of the vessel or in the case where a sheath is used through the sheath of the introducer kit.

The sheath 83 is then removed from the vessel. A preferred method for removing the sheath 83 is to use a sheath which can be peeled apart while it is being withdrawn from the vessel 72. This step is illustrated in FIG. 15j. This permits the sheath to be removed without releasing control of the tether 29.

Finally, the tether 29 is surgically tied to the muscle tissue 78 surrounding the vessel 72. The prosthesis 21 is now positioned within the lumen 36 of a vessel 72 with the end 28 of the prosthesis 21 in the downstream direction of blood flow in the vessel 72 and with the tether 29 anchoring the prosthesis 21 so that the prosthesis 21 will be free to move within the lumen 36 of the vessel. When the prosthesis 21 is anchored in this fashion, blood flows over the inside surface 24 and the outside sur 23 of the prosthesis 21 exposing the thrombogenic surf of the prosthesis 21 to a continuous blood flow and encouraging impregnation of the thrombogenic surface by collagenous tissue.

The vessel, since it is a relatively low pressure blood vessel, can be easily closed surgically and will heal very quickly so that the patient will lose little or no blood and will encounter little or no stress from the surgical procedure to implant the prosthetic device 21.

The prosthesis 21 is left in place in the vessel for a sufficient period of time to permit collagenous tissue to grow on the thrombogenic surface of the prosthetic device 21. Where the prosthetic device or prosthesis 21 utilizes a mesh 53 as illustrated in FIG. 8 of the drawings, the collagenous tissue will impregnate the mesh 53 supported by the outside surface 23 of the substrate 22 to generate a tube of collagenous tissue having physical characteristics very similar to the inside wall 73 of the vessel wall 72. Experience has demonstrated that the prosthesis need only be left in the vessel for about 6 to about 8 weeks to generate a homograft 32 having a wall thickness adequate for transplant purposes.

The third phase of the production occurs at the end of about a 6 to 8 week period. The prosthetic device now having a homograft generated on the selected thrombogenic surface is then removed from the lumen of the vessel by a simple surgical procedure which involves surgical removal of the prosthetic device 21 from the vessel along with the tether 29. The procedure is a very simple procedure which exposes the host to very slight surgical risk and produces a homograft which is fully compatible with the patient's body tissues and which is extremely useful in making implants to replace vessels and arteries of the patient's body.

After the prosthetic device is removed, the homograft 32 is then removed from the substrate 22 as previously described by removing the end portions of the substrate 22 leaving a uniform tubular shaped homograft 32. If desired, the homograft 32 can then be inverted as described in connection with FIG. 9 of the drawings in order to reverse the surfaces of the homograft and positioned the surface exposed to the greatest blood flow within the homograft to, thereby, prepare the homograft for transplant in the patient.

When a mesh material 53 is utilized in the formation of the homograft, the surgeon can then place the homograft in the patient's body by suturing the homograft to existing vessels and arteries through the ends of the mesh material thus strengthening the sutured connection.

The invention has been described in connection with specific references to materials and processes. Variations can be made to the invention without departing from the spirit and scope thereof. For example, the substrate 22 can be composed of a variety of materials. Choices may be made dependent upon which surfaces need to be thrombogenic and which need to be non-thrombogenic in order to produce a homograft of the desired characteristics.

A variety of sizes of homografts can be generated depending upon the diameter of the artery or vessel which needs to be repaired. Selection of a vessel for the purpose of generating the homograft may vary according to the needs of the patient. As an example, a vessel other than the femoral vessel might be utilized as the site for generating the homograft. It has been found that excellent results and safety to the host can be achieved by using a vessel with a lumen of sufficient diameter that the diameter of prosthesis 21 is only about two-thirds the diameter of the lumen. Smaller or larger vessels may be selected depending upon the needs of the patient. The process for making an incision in the vessel for inserting the prosthesis is not critical. The important aspect of the process is to suspend the prosthesis in the presence of blood flow so that blood can flow along the longitudinal length of the substrate 22 to expose a thrombogenic surface of the substrate prosthesis 21 to an adequate blood flow to generate a healthy and strong homograft. These and other variations can be made to the invention without departing from spirit and scope thereof.

What is claimed is:

1. A prosthetic device for promoting controlled collagenous tissue growth when suspended in the lumen of a blood vessel in the presence of blood flow which comprises:
    (a) Tubular substrate means having a generally cylindrical outside surface and a generally cylindrical inside surface terminating at first and second open ends to permit blood flow along said inside surface,
    (b) At least one of said surfaces being a thrombogenic surface to promote growth of collagenous tissue along such thrombogenic surface and
    (c) Tether means for positioning the tubular substrate means within the lumen so as to allow fluid flow within the lumen to contact both the inside and outside surfaces of the tubular substrate means, said tether means having a first attachment to the substrate means and a second attachment, spaced apart from the first attachment, for attaching to the lumen.

2. A device in accordance with claim 1 in which said substrate means is made from polyurethane.

3. A device in accordance with claim 1 in which said thrombogenic surface is said inside surface.

4. A device in accordance with claim 1 in which said thrombogenic surface is said outside surface.

5. A device in accordance with claim 1 in which said tether means is a flexible tether.

6. A prosthesis for promoting controlled collagenous tissue growth when suspended in the lumen of a vessel in the presence of blood flow which comprises:
   (a) Tubular substrate means having a generally cylindrical outside surface and a generally cylindrical inside surface terminating at first and second open ends to permit blood flow along said inside surface,
   (b) Said inside and outside surfaces being thrombogenic to promote growth of collagenous tissue along such thrombogenic surfaces, and
   (c) Tether means for positioning the tubular substrate means within the lumen so as to allow fluid flow within the lumen to contact both the inside and outside surfaces of the tubular substrate means, said tether means having a first attachment to the substrate means and a second attachment, spaced apart from the first attachment, for attaching to the lumen.

7. A device for promoting controlled collagenous tissue growth when suspended in the lumen of a vessel in the presence of blood flow which comprises:
   (a) A tube of thrombogenic mesh material,
   (b) Tubular substrate means for supporting said mesh material, said tubular substrate means having a generally cylindrical outside surface and a generally cylindrical inside surface terminating at first and second open ends to permit blood flow along said mesh material extending from said first end to said second end of said substrate means,
   (c) Contact means at said first and second ends for connecting said tube of mesh material at each end of said substrate means to immobilize said mesh material between said first and second ends, and
   (d) Tether means for positioning the tubular substrate means within the lumen so as to allow fluid flow within the lumen to contact both the inside and outside surfaces of the tubular substrate means, said tether means having a first attachment to the substrate means and a second attachment, spaced apart from the first attachment, for attaching to the lumen.

8. A device in accordance with claim 7 in which said mesh material is selected from a group consisting of Dacron, monofilament nylon, silicon polyester fiber, silk, or polypropylene.

9. A device in accordance with claim 7 in which said tether means is a flexible tether.

10. A device in accordance with claim 9 in which said tether is made of a material selected from the group consisting of Dacron braid, monofilament nylon braid, silicon polyester fiber braid, silk braid or polypropelene braid.

11. A device in accordance with claim 7 in which said substrate is polyurethane.

12. A device in accordance with claim 7 in which said mesh material extends from said first end to said second end of said substrate means to enclose said substrate means generally along said outside surface.

13. A device in accordance with claim 12 in which said mesh is connected at said first and second ends to provide a loose fit of said mesh over said outside surface to permit blood flow between said mesh material and said outside surface.

14. A device in accordance with claim 7 in which said mesh material extends from said first end to said second end along said inside surface and in which said mesh is stretched along a longitudinal axis through said first and second ends to position the mesh along the length of said inside surface generally out of contact with said inside surface.

15. A device in accordance with claim 7 in which said substrate is composed of a non-thrombogenic material.

16. A device in accordance with claim 15 in which said substrate is composed of a non-thrombogenic material selected from the group consisting of carbon, cardiothane, avcothane, coated material, albumin coated material and polyurethane.

17. A device in accordance with claim 7 in which said substrate is coated on said outside and inside surfaces with a non-thrombogenic coating.

18. A device in accordance with claim 17 in which said coating is carbon coated.

* * * * *